United States Patent [19]

Wiechert et al.

[11] 4,180,570
[45] Dec. 25, 1979

[54] 17β-HYDROXY-4-ANDROSTEN-3-ONES AND PROCESS FOR THE PREPARATION THEREOF

[75] Inventors: Rudolf Wiechert; Dieter Bittler; Ulrich Kerb; Jorge Casals-Stenzel; Wolfgang Losert, all of Berlin, Fed. Rep. of Germany

[73] Assignee: Schering Aktiengesellschaft, Berlin and Bergkamen, Fed. Rep. of Germany

[21] Appl. No.: 904,694

[22] Filed: May 10, 1978

[30] Foreign Application Priority Data

May 16, 1977 [DE] Fed. Rep. of Germany ....... 2722705
May 16, 1977 [DE] Fed. Rep. of Germany ....... 2722706

[51] Int. Cl.² .................................................. C07J 1/00
[52] U.S. Cl. ............................... 424/243; 260/397.4; 260/239.55 R; 260/239.55 C; 260/397.5; 260/239.57
[58] Field of Search .................. 260/397.4, 239.55; 424/243

[56] References Cited
U.S. PATENT DOCUMENTS 4,016,269 4/1977 Hofmeister et al. ......... 260/239.55 R
4,118,488 10/1978 Phillippson et al. .............. 260/397.1

Primary Examiner—Elbert L. Roberts
Attorney, Agent, or Firm—Millen & White

[57] ABSTRACT

Compounds of the formula I

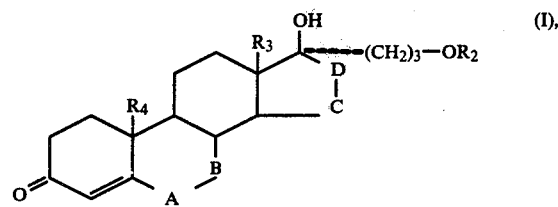

wherein
$R_2$ is hydrogen or an organic acid residue;
$R_3$ is methyl or ethyl;
$R_4$ is hydrogen or methyl;

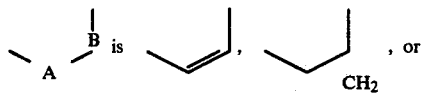

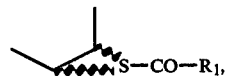

wherein $R_1$ is lower alkyl; and

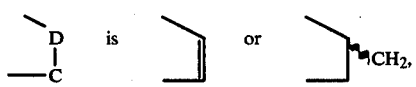

and when $R_2$ is a dibasic acid residue, the physiologically acceptable salts thereof with the free acid moiety of the $R_2$ group, are physiologically active, e.g., are diuretics having aldosterone antagonist effects.

28 Claims, No Drawings

17β-HYDROXY-4-ANDROSTEN-3-ONES AND PROCESS FOR THE PREPARATION THEREOF

BACKGROUND OF THE INVENTION

This invention relates to physiologically active steroid compounds.

SUMMARY OF THE INVENTION

It is an object of this invention to provide such compounds which especially are useful as diuretics of the aldosterone antagonist type.

Upon further study of the specification and claims, further objects and advantages of this invention will become apparent to those skilled in the art.

These objects have been acheived by providing 17β-hydroxy-4-androsten-3-ones of Formula I

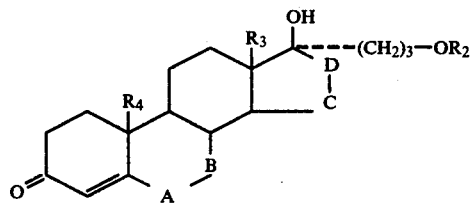

wherein
$R_2$ is hydrogen or an organic acid residue,
$R_3$ is methyl or ethyl,
$R_4$ is hydrogen or methyl,

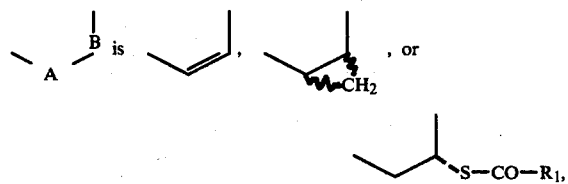

wherein $R_1$ is lower alkyl, and

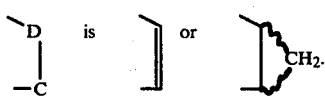

Physiologically compatible salts of such compounds, e.g., of the acid residue when the latter is a dibasic salt, are also included.

DETAILED DISCUSSION

Suitable organic acid residues $R_2$ include all those derived from conventional physiologically compatible acids.

In particular, preferred such acid residues are the monovalent acyl radicals of carboxylic acids, preferably monobasic and dibasic hydrocarbon carboxylic acids, of up to 18 carbon atoms, preferably 2–8 carbon atoms, e.g., monobasic acyclic aliphatic carboxylic acids, such as formic, acetic, propionic, butyric, isobutyric, α-ethylbutyric, pivalic, valeric, isovaleric, α-ethylvaleric, trimethyacetic, 2-methylbutyric, 3-ethylbutyric, caproic, triethylacetic, enanthic and caprylic acids; cyclic carboxylic acids of 3–8 carbon atoms, preferably $C_{3-8}$ cycloaliphatic acids, such as cyclopropylideneacetic, cyclobutylcarboxylic, cyclopentylcarboxylic, cyclopentylacetic, β-cyclopentylpropionic, cyclohexylcarboxylic and cyclohexylacetic acids; and carbocyclic aryl carboxylic acids, e.g., benzoic or naphthoic acids, or ar($C_{1-4}$)alkyl acids, wherein aryl is similarly defined, such as 2-, 3- or 4-methylbenzoic acid; and the like.

Other examples of suitable $R_2$ groups are the acyl radicals of tetradecanoic, hexadecanoic, octadecanoic, palmitic, stearic, and β-cyclohexylpropionic acids, 2,3-, 2,4-, 2,6-, 3,4-, and 3,5-dimethylbenzoic, ethylbenzoic, naphthoic, 3-methyl-α-naphthoic, β-phenylpropionic, diphenylacetic, and α-naphthyl-acetic acids; dibasic alkanoic acids, such as, for example, oxalic, maleic, fumaric, succinic, malonic, glutaric, α-methyl-glutaric, β-methylglutaric, β,β-dimethylglutaric, adipic, pimelic and sebacic acids; and dibasic aromatic acids, such as those which can form inner anhydrides, such as phthalic acid.

Since the chemical character of the acid residue $R_2$ is not critical for achieving the properties of the compounds of this invention, contemplated equivalents of the compounds of Formula I are those wherein $R_2$ is the acyl radical of any other non-toxic acid which forms an ester with the primary 17α-hydroxy group. Thus, also suitable are other aliphatic, araliphatic and aromatic non-hydrocarbon carboxylic acids of up to 18 carbon atoms, preferably 2–8 carbon atoms. Such acids can be unsubstituted or substituted; mono-, di-, or polybasic; cyclic, heterocyclic or acyclic; and saturated or unsaturated.

Examples of such equivalent acids are carbamic acids, such as carbamic, phenylcarbamic, n-butylcarbamic, dimethylcarbamic, diethylcarbamic and allophanic acids; or heterocyclic acids, e.g., preferably monocyclic ones containing 4–7 ring atoms of which 1–3 can be hetero atoms, e.g., O, N or S, preferably O or N, such as β-furylcarboxylic, pyrrolecarboxylic, β-pyrrolidinopropionic, N-methylpyrrolidino-2-carboxylic and pyrrole-2-carboxylic acids.

The $R_2$ acyl radicals can also be substituted by one or several substituents.

Examples of suitable substituents include the following residues: hydroxy, halo (F, Cl, Br or I), $C_{1-4}$ alkoxy, acyloxy, sulfonyloxy, amido, sulfato, nitro, mercapto, and cyano. Suitable acyloxy groups include residues of glycolic, lactic, citric, tartaric, maleic, glyceric, mannonic, gluconic and salicylic acids; and residues of amino acids, such as glycine, aminopropionic acid, diglycolamino and triglycolamino acids, methylglycine, dimethylglycine, diethylglycine, p-aminosalicylic acid and p-aminobenzoic acid; and ethylmercaptoacetic acid, benzylmercaptoacetic, chloroacetic, fluoroacetic, trichloroacetic, trifluoroacetic, thioglycolic, m-nitrobenzoic, 2,3,4-trimethoxybenzoic, phenoxyacetic and α-naphthoxyacetic acids.

Especially suitable are, above all, the dibasic, saturated and unsaturated carboxylic acids.

The salts of this invention are derived from the corresponding hemiacylates of these dibasic acids. Particularly suitable as the cations are the alkali metals sodium and potassium, as well as ammonium. However, likewise suitable are the bivalent alkaline earth metals, such as calcium, wherein, of course, 2 mole equivalents of hemiacylate are present per one mole equivalent of calcium.

Lower alkyl residues $R_1$ are those of up to 5 carbon atoms, such as methyl, ethyl, propyl, n-butyl, isobutyl, tert-butyl and n-pentyl.

The present invention furthermore relates to a process for the preparation of the compounds of Formula I, comprising conventionally treating 3-keto-4,6-androstadiene spirolactones of Formula II

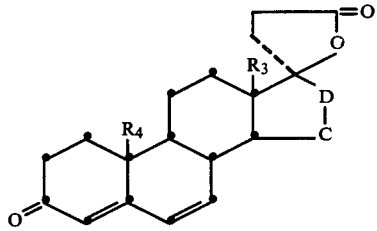

wherein —C—D—, $R_3$ and $R_4$ are as defined for Formula I, with lithium aluminum hydride in an aprotic solvent, wherein the 3-keto group is previously protected by a blocking group; and (a) when —A—B— of Formula I is to be a

group, carrying out a reaction in a conventional manner with a thioalkanoic acid in a protonic organic solvent or mixtures of such solvents, optionally in the presence of a solubilizer; or (b) when —A—B— of Formula I is to be a

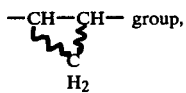

introducing a methylene group in a conventional manner with dimethyl sulfoxonium methylide in dimethyl sulfoxide as the solvent; and when $R_2$ is an acid residue, carrying out an esterification in a conventional manner with the addition of an esterification catalyst; and optionally partially saponifying the thus-obtained ester and, if desired, esterifying with the finally desired acid, and optionally converting the same into a suitable salt.

A suitable embodiment of the process of this invention for the case wherein $R_2$ is the residue of a dibasic acid involves converting the hemiacylate into an ammonium, alkali metal, or alkaline earth metal salt.

To prepare the compounds of this invention of Formula I wherein —A—B— is a double bond, the spirolactone of Formula II is advantageously provided intermediarily with a blocking group in the 3-position. Ketalization with ethylene glycol is well suited for this purpose.

In this method, the $\Delta^{4,6}$-3-keto steroid of Formula II is dissolved in a suitable solvent, such as methylene chloride, and the ethylene glycol and the triethyl ester of orthoformic acid are allowed to react in the presence of a catalyst, such as p-toluenesulfonic acid, advantageously under slight heating to above room temperature. The thus-obtained $\Delta^{4,6}$-3,3-ethylenedioxy steroid is dissolved in an inert solvent, such as tetrahydrofuran or dioxane, and treated suitably under cooling with lithium aluminum hydride; in ths step, the temperature should not exceed room temperature.

In the acidic working-up operation, the blocking group is subsequently split off again.

To produce the compounds of this invention of Formula I wherein the group —S—CO—$R_1$, wherein $R_1$ is as defined above, is present in the 7α-position, the corresponding 17β-hydroxy-$\Delta^{4,6}$-steroid of Formula I is dissolved in a protonic solvent or in a mixture thereof; then a thioalkanoic acid of the formula HS—COR$_1$ is added thereto, wherein $R_1$ is as defined above. The reaction mixture is heated to temperatures of from above room temperature up to the boiling temperature of the solvent. Suitable solvents and/or mixtures thereof include methanol, acetone, and tetrahydrofuran. Solubilizers, which may be employed, such as diisopropyl ether, benzene, and heptane, do not interfere with the progress of the reaction.

In order to produce the compounds of this invention of Formula I having a methylene group in the 6,7-position, the corresponding $\Delta^{4,6}$-steroid of general Formula I is suitably and conventionally treated with dimethyl sulfoxonium methylide to introduce the methylene group. For this purpose, the $\Delta^{4,6}$-steroid is added gradually under a protective gas atmosphere, such as nitrogen or argon, either to a suspension of trimethyl sulfoxonium iodide with sodium hydride in a mineral oil and dimethyl sulfoxide or to a solution of trimethyl sulfoxonium iodide and sodium hydroxide in dimethyl sulfoxide. The reaction is terminated at 20°-40° C. after 10–30 hours. The reaction product is extracted, and the 6β,7β-methylene compound is conventionally separated from the simultaneously formed 6α,7α-methylene compound.

The esterification of the primary hydroxy group in the side chain in the 17α-position takes place according to conventional methods. One such suitable method is, for example, the reaction with an acid anhydride or acid halogenide in the presence of a tertiary amine, such as, for example, pyridine, collidine, triethylamine, or 4-dimethylaminopyridine, at room temperature or thereabove. The hydroxy group can also be esterified with an acid anhydride using a strong acid, such as p-toluenesulfonic acid or using the corresponding acid and trifluoroacetic anhydride or using a heavy metal salt of the corresponding acid, e.g., lead acetate, in the presence of the corresponding acid anhydride, such as acetic anhydride.

Saponifications are suitably conducted under gentle conditions, such as with methanolic potassium hydroxide solution without heating.

It is also possible to simultaneously esterify the primary hydroxy group during the introduction of the 7-acylthio group. For this purpose, the reaction is conducted with the desired thio acid under heating, without the use of any other solvent.

If the primary hydroxy group has been esterified with a dibasic acid, the hemiacylate can be converted into the desired alkali salt by reaction, for example, with a methanolic potassium methylate or sodium methylate solution. To prepare the ammonium salt, a solution of ammonia in methanol is advantageously used.

The reaction products of this invention are separated by following conventional methods, such as precipitation, filtration, or extraction, and purified, for example, by chromatography and/or recrystallization.

PREPARATION OF STARTING MATERIALS

The starting material 3-oxo-4,6,15-androstatriene[17(β-1')-spiro-5']-perhydrofuran-2'-one can be prepared as follows:

20.0 g. of 3β-hydroxy-5,15-androstadien-17-one is combined in 280 ml. of absolute tetrahydrofuran with 4.34 g. of freshly pressed lithium. Then, under ice cooling, 36 ml. of 1-bromo-3-dimethoxypropane is added dropwise within 30 minutes. After 1.5 hours of agitation at ice bath temperature, the mixture is filtered off from the unreacted lithium, and the filtrate is stirred into ice water. The precipitate is filtered off, washed with water, and taken up in methylene chloride.

After drying and evaporation, the residue is chromatographed on silica gel, thus obtaining 19.9 g. of 17α-(3'-dimethoxypropyl)-5,15-androstadiene-3β,17β-diol as an oil.

19.9 g. of 17α-(3'-dimethoxypropyl)-5,15-androstadiene-3β,17β-diol is combined in 500 ml. of acetone under ice cooling with 1.0 g. of p-toluenesulfonic acid and further stirred for 15 minutes under cooling. The mixture is then stirred into ice water which contains sodium bicarbonate; the precipitate is filtered off, washed, and taken up in methylene chloride. After drying and evaporation, 19.2 g. of crude 3β-hydroxy-5,15-androstadiene[17(β-1')-spiro-5']perhydrofuran 2'ξ-methyl ether is obtained as an oil.

19.2 g. of 3β-hydroxy-5,15-androstadiene[17(β-1')-spiro-5']perhydrofuran 2'ξ-methyl ether is combined in 394 ml. of absolute toluene and 39.4 ml. of cyclohexanone with 3.94 g. of aluminum isopropylate in 40 ml. of absolute toluene and heated for 45 minutes under gradual distillation. The mixture is then diluted with methylene chloride, washed with dilute sulfuric acid and water, dried, and evaporated. The residue is chromatographed on silica gel, thus obtaining 17.5 g. of 3-oxo-4,15-androstadiene[17(β-1')-spiro-5']perhydrofuran 2'ξ-methyl ether as an oil.

UV: $\epsilon_{239} = 16,200$.

17.5 g. of 3-oxo-4,15-androstadiene[17(β-1')-spiro-5']perhydrofuran 2'ξ-methyl ether is combined in 350 ml. of acetone under ice cooling with 35 ml. of chromosulfuric acid (prepared from 267 g. of CrO$_3$, 400 ml. of water, and 230 ml. of concentrated sulfuric acid, filled up with water to a volume of 1 liter) and stirred for 30 minutes under ice bath cooling. The mixture is then stirred into ice water; the precipitate is filtered off, washed with water, and taken up in methylene chloride. After drying and evaporation, the residue is chromatographed on silica gel, thus obtaining 11.8 g. of 3-oxo-4,15-androstadiene[17(β-1')-spiro-5']perhydrofuran-2'-one. A sample recrystallized from diisopropyl ether/acetone melts at 189.5°–191.5° C.

UV: $\epsilon_{240} = 17,300$.

10.0 g. of 3-oxo-4,15-androstadiene[17(β-1')-spiro-5']perhydrofuran-2'-one is combined in 100 ml. of absolute dioxane with 10 ml. of the triethyl ester of orthoformic acid and 10 ml. of dioxane/concentrated sulfuric acid (prepared from 13.5 ml. of absolute dioxane and 0.48 ml. of concentrated sulfuric acid). The mixture is stirred for 30 minutes at room temperature, combined with 2 ml. of pyridine, and diluted with ether. The ether phase is washed with water, dried, and evaporated. The residue is triturated with pyridine-containing methanol, the thus-separated crystals are vacuum-filtered, and the product is 8.9 g. of 3-ethoxy-3,5,15-androstatriene[17(β-1')-spiro-5']perhydrofuran-2'-one, m.p. 153.5°–159° C.

UV: $\epsilon_{240} = 19,800$.

8.9 g. of 3-ethoxy-3,5,15-androstatriene[17(β-1')-spiro-5']perhydrofuran-2'-one is dissolved in 201 ml. of acetone, cooled in an ice bath, and combined with 1.38 ml. of pyridine, 6.36 g. of sodium acetate, and 63.6 ml. of water. Then, 4.72 g. of N-bromosuccinimide is added thereto, and 6.36 ml. of acetic acid is added dropwise during 15 minutes. The mixture is stirred for 45 minutes under ice cooling, diluted with ether, and washed neutral with water. After drying and evaporation, 10.35 g. of 6β-bromo-3-oxo-4,15-androstadiene[17(β-1')-spiro-5']perhydrofuran-2'-one is obtained as an oil.

UV: $\epsilon_{245} = 12,700$.

10.35 g. of 6β-bromo-3-oxo-4,15-androstadiene[17(β-1')-spiro-5']perhydrofuran-2'-one is stirred in 103.5 ml. of dimethylformamide with 4.67 g. of lithium carbonate and 5.37 g. of lithium bromide for 18 hours at 100° C. Then the mixture is stirred into ice water, the precipitate is filtered off, washed with water, and taken up in methylene chloride. After drying and evaporation, the residue is chromatographed. Recrystallization from diisopropyl ether/acetone yields 6.5 g. of 3-oxo-4,6,15-androstatriene[17(β-1')-spiro-5']-perhydrofuran-2'-one, m.p. 182.5°–184.5° C.

UV: $\epsilon_{284} = 27,100$.

The starting material 15α,16α-methylene-3-oxo-4,6-androstadiene[17(β-1')-spiro-5']perhydrofuran-2'-one can be made as follows:

15 g. of 3β-hydroxy-15α,16α-methylene-5-androsten-17-one (prepared, for example, in accordance with DOS [German Unexamined Laid-Open Application] No. 2,109,555) is combined under ice cooling in 150 ml. of absolute tetrahydrofuran with 3.6 g. of lithium, and then 30 ml. of 1-bromo-3-dimethoxypropane is added dropwise thereto within 30 minutes. After agitation for 2.5 hours at ice bath temperature, the mixture is separated from the unreacted lithium and the filtrate stirred into ice water. The thus-obtained precipitate is filtered off, washed with water, and taken up in methylene chloride. After drying and evaporation the residue is chromatographed on silica gel, thus obtaining 16.8 g. of 17α-(3'-dimethoxypropyl)-15α,16α-methylene-5-androstene-3β,17β-diol. A sample recrystallized from diisopropyl ether/acetone melts at 153°–159° C.

16.5 g. of 17α-(3'-dimethoxypropyl)-15α,16α-methylene-5-androstene-3β,17β-diol is stirred in 410 ml. of 70% acetic acid for 18 hours at room temperature. The mixture is then stirred into ice water, the thus-obtained precipitate is filtered off, taken up in chloroform, and washed with sodium bicarbonate solution and water. After drying and evaporation, the residue is chromatographed on silica gel, thus producing 11.5 g. of 3β-hydroxy-15α,16α-methylene-5-androstene[17(β-1')-spiro-5']perhydrofuran-2'ξ-ol. A sample recrystallization from diisopropyl ether/acetone melts at 194°–202° C.

10.5 g. of 3β-hydroxy-15α,16α-methylene-5-androstene[17(β-1')-spiro-5']perhydrofuran-2'ξ-ol is combined in 210 ml. of absolute toluene with 21 ml. of cyclohexanone and 2.1 g. of aluminum isopropylate in 20 ml. of absolute toluene and heated for 45 minutes under gradual distillation. The mixture is then diluted with methylene chloride, washed with 2 N sulfuric acid and water, dried, and evaporated, thus obtaining 11.5 g. of crude 15α,16α-methylene-3-oxo-4-androstene[17(β-1')-spiro-5']perhydrofuran-2'ξ-ol as an oil. A sample purified by preparative layer chromatography and recrystallization from diisopropyl ether/acetone melts at 259°–268° C.

UV: $\epsilon_{241} = 16,500$.

10.5 g. of 15α,16α-methylene-3-oxo-4-androstene[17(β-1')-spiro-5']perhydrofuran-2'ξ-ol is combined in 100 ml. of acetone under ice cooling with 10 ml. of chromosulfuric acid (prepared from 267 g. of CrO$_3$, 400 ml. of water, and 230 ml. of concentrated sulfuric acid, filled up to 1 liter with water), and stirred for one hour. The mixture is then stirred into ice water, washed with water, and taken up in methylene chloride. After drying and evaporation, the residue is chromatographed on silica gel, thus obtaining 8.2 g. of 15α,16α-methylene-3-oxo-4-androstene[17(β-1')-spiro-5']perhydrofuran-2'-one. A sample recrystallized from diisopropyl ether/acetone melts at 180°–181° C.

UV: $\epsilon_{240} = 16,600$.

7.2 g. of 15α,16α-methylene-3-oxo-4-androstene[17-(β-1')-spiro-5']perhydrofuran-2'-one is combined in 72 ml. of absolute dioxane and 7.2 ml. of the triethyl ester of orthoformic acid with a solution of 7.2 ml. of absolute dioxane and 0.26 ml. of concentrated sulfuric acid and agitated for 30 minutes at room temperature. Then, 2 ml. of pyridine is added to the mixture, and the latter is diluted with ether, washed with water, and dried. Evaporation yields 8.5 g. of crude 3-ethoxy-15α,16α-methylene-3,5-androstadiene[17(β-1')-spiro-5']perhydrofuran-2'-one.

UV: $\epsilon_{241} = 15,700$.

8.5 g. of 3-ethoxy-15α,16α-methylene-3,5-androstadiene[17(β-1')-spiro-5']perhydrofuran-2'-one is dissolved in 192 ml. of acetone, cooled in an ice bath, combined with 1.32 ml. of pyridine, 6.08 g. of sodium acetate, and 60.8 ml. of water, and then 4.51 g. of N-bromosuccinimide is added to the mixture and, within 10 minutes, 6.08 ml. of acetic acid is introduced dropwise. The mixture is stirred for 1 hour at ice bath temperature, diluted with ether, washed with water, and dried. Evaporation yields 9.6 g. of crude 6β-bromo-3-oxo-4-androstene[17(β-1')-spiro-5']perhydrofuran-2'-one.

9.6 g. of 6β-bromo-3-oxo-4-androstene[17(β-1')-spiro-5']perhydrofuran-2'-one is agitated in 96 ml. of dimethylformamide with 3.75 g. of lithium carbonate and 4.4 g. of lithium bromide for 18 hours at 100° C. The mixture is then stirred into ice water, the thus-obtained precipitate is filtered off, taken up in methylene chloride, washed with 2 N sulfuric acid and water, and dried. After evaporation, the residue is chromatographed on silica gel, thus obtaining 6.5 g. of 15α,16α-methylene-3-oxo-4,6-androstadiene[17(β-1')-spiro-5']perhydrofuran-2'-one. A sample recrystallized from diisopropyl ether melts at 180.5°–182.5° C.

UV: $\epsilon_{283} = 26,300$.

The starting material 15β,16β-methylene-3-oxo-4,6-androstadiene[17(β-1')-spiro-5']perhydrofuran-2'-one can be produced as described below:

15 g. of 3β-hydroxy-15β,16β-methylene-5-androsten-17-one (prepared, for example, according to German Pat. No. 1,593,500) is reacted in 150 ml. of absolute tetrahydrofuran with 3.27 g. of lithium and 29 ml. of 1-bromo-3-dimethoxypropane for 2 hours at ice bath temperature and for 4 hours at room temperature. The mixture is filtered off from the unreacted lithium; the filtrate is stirred into ice water, the precipitate is filtered off and taken up in methylene chloride. After drying and evaporation, the residue is chromatographed on silica gel, thus obtaining 17.4 g. of 17α-(3'-dimethoxypropyl)-15β,16β-methylene-5-androstene-3β,17β-diol.

17.0 g. of 17α-(3'-dimethoxypropyl)-15β,16β-methylene-5-androstene-3β,17β-diol is stirred in 340 ml. of 70% acetic acid for 18 hours at room temperature. The mixture is stirred into ice water, the thus-produced precipitate is filtered off and taken up in methylene chloride. The methylene chloride phase is washed with sodium bicarbonate solution and water, dried, and evaporated, thus producing 13.8 g. of 3β-hydroxy-15β,16β-methylene-5-androstene[17(β-1')-spiro-5']perhydrofuran-2'ξ-ol as a crude product.

8.8 g. of 3β-hydroxy-15β,16β-methylene-5-androstene-[17(β-1')-spiro-5']perhydrofuran-2'ξ-ol is combined in 176 ml. of absolute toluene and 17.6 ml. of cyclohexanone with 1.76 g. of aluminum isopropylate in 50 ml. of absolute toluene and heated for 3 hours under gradual distillation. The mixture is then diluted with ether, washed with 2 N sulfuric acid and water, dried, and evaporated. The residue is chromatographed on silica gel, thus obtaining 4.3 g. of 15β,16β-methylene-3-oxo-4-androstene[17(β-1')-spiro-5']perhydrofuran-2'-one. A sample recrystallized from diisopropyl ether/acetone melts at 178.5°–179.5° C.

UV: $\epsilon_{241} = 16,500$.

4.2 g. of 15β,16β-methylene-3-oxo-4-androstene[17(β-1')-spiro-5']perhydrofuran-2'-one is refluxed for 18 hours in 84 ml. of tertiary butanol with 4.2 g. of chloranil. The solvent is distilled off under vacuum, and the residue is chromatographed on silica gel. To further purify the product, preparative layer chromatography is utilized, thus obtaining 1.1 g. of 15β,16β-methylene-3-oxo-4,6-androstadiene[17(β-1')-spiro-5']perhydrofuran-2'-one as an oil.

UV: $\epsilon_{284} = 25,700$.

If 17β-hydroxy-17α-(3-hydroxypropyl)-15α,16α-methylene-4,6-androstadien-3-one is utilized as the starting material, this compound can also be obtained as follows:

11.0 g. of 3β-hydroxy-15α,16α-methylene-5-androsten-17-one (prepared according to German Pat. No. 2,109,555) is combined in 300 ml. of absolute tetrahydrofuran with 4.8 g. of lithium and 60 ml. of 1-bromo-3-(tetrahydropyran-2-yloxy)propane and heated for 2.5 hours under reflux. After cooling, the mixture is separated from the unreacted lithium and precipitated into ice water. The precipitate is filtered off, taken up in methylene chloride, the organic phase washed with water, dried over sodium sulfate, and evaporated under vacuum. The residue is chromatographed on silica gel, thus obtaining 16.8 g. of 15α,16α-methylene-17α-[3-(tetrahydropyran-2-yloxy)propyl]-5-androstene-3β,17β-diol. A sample recrystallized from diisopropyl ether melts at 147.5°–149.5° C.

15.8 g. of 15α,16α-methylene-17α-[3-(tetrahydropyran-2-yloxy)propyl]-5-androstene-3β,17β-diol is heated to boiling in 316 ml. of toluene and 31.6 ml. of cyclohexanone and combined with a solution of 3.16 g. of aluminum isopropylate in 30 ml. of toluene. Thereafter, the mixture is stirred for another 45 minutes under gradual distillation. After cooling, the mixture is diluted with ether, washed with dilute sulfuric acid and water, dried, and evaporated. The residue is chromatographed on silica gel, thus obtaining 12.0 g. of 17β-hydroxy-15α,16α-methylene-17α-[3-(tetrahydropyran-2-yloxy)-propyl]-4-androsten-3-one.

UV: $\epsilon_{242} = 15,900$.

800 mg. of 17β-hydroxy-15α,16α-methylene-17α-[3-(tetrahydropyran-2-yloxy)propyl]-4-androsten-3-one is heated in 16 ml. of methanol and 3.2 ml. of water with 400 mg. of oxalic acid for one hour under reflux. The reaction mixture is diluted with ether, washed neutral with water, dried, and evaporated. The residue is recrystallized from diisopropyl ether/acetone, thus producing 450 mg. of 17β-hydroxy-17α-(3-hydroxypropyl)-15α,16α-methylene-4-androsten-3-one, m.p. 187.5°–188.5° C.

UV: $\epsilon_{242} = 16,200$.

10.0 g. of 17α-hydroxy-15α,16α-methylene-17α-[3-(tetrahydropyran-2-yloxy)propyl]-4-androsten-3-one is heated under reflux in 100 ml. of tert.-butanol with 10.0 g. of chloranil for 18 hours. The mixture is filtered off from the precipitate, which has formed (hydroquinone and unreacted chloranil); the filtrate is diluted with ether, washed with sodium bicarbonate solution and water, dried, and evaporated, thus obtaining 10 g. of crude 17β-hydroxy-15α, 16α-methylene-17α-[3-(tetrahydropyran-2-yloxy)propyl]-4,6-androstadien-3-one.

UV: $\epsilon_{285} = 18,500$.

10 g. of crude 17β-hydroxy-15α,16α-methylene-17α-[3-(tetrahydropyran-2-yloxy)propyl]-4,6-androstadien-3-one is heated under reflux in 200 ml. of methanol and 40 ml. of water with 5.0 g. of oxalic acid for 1 hour. The mixture is then stirred into ice water, the precipitate is filtered off and taken up in methylene chloride; the organic phase is washed with water, dried and evaporated under vacuum. The residue is chromatographed on silica gel, thus obtaining 7.5 g of 17β-hydroxy-17α-(3-hydroxypropyl)-15α,16α-methylene-4,6-androstadien-3-one. A sample recrystallized from diisopropyl ether/acetone melts at 180.5°–181.5° C.

UV: $\epsilon_{285} = 26,900$.

The compounds of this invention possess pharmacologically valuable properties. For example, inter alia, they are diuretics of the aldosterone antagonist type, i.e., they reverse the effect of desoxycorticosterone on the elimination of sodium and potassium in mammals, including humans. The compounds of this invention have proven to be surprisingly superior to the conventional potassium Canrenoate in their activity in the test model of Hollmann (G. Hollmann et al, "Tubulaere Wirkungen and renale Elimination von Spirolactonen" [Tubular Effects and Renal Elimination of Spirolactones] Naunyn-Schmiedeberg's Arch. Exp. Path. Pharmak. 247 (1964):419; and P. Marx, "Renale Wirkungen des d-Aldosterons und seines Antagonisten Spirolacton" [Renal Effects of d-Aldosterone and Its Antagonist Spironolactone], Disseration at the Medical Faculty of Free University of Berline 1966).

The pharmacologically active compounds of Formula I can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10–100 mg. in a pharmaceutically acceptable carrier per unit dosage.

The dosage of the compounds according to this invention is 20–500 mg./day when administered to human patients as a diuretic, in the same manner as the known aldosterone antagonists spironolactone or potassium Canrenoate.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. All temperatures are set forth in degress Celsius.

EXAMPLE 1

12.0 g. of 3-oxo-4,6,15-androstatriene[17(β-1')-spiro-5']perhydrofuran-2'-one is combined in 60 ml. of methylene chloride with 36 ml. of ethylene glycol, 24 ml. of the triethyl ester of orthoformic acid, and 120 mg. of p-toluenesulfonic acid and agitated for 75 minutes at 50°. The reaction solution is then combined with 3 ml. of pyridine, diluted with ether, washed with water, dried, and evaporated to dryness under vacuum, thus obtaining 13.5 g. of crude 3,3-ethylenedioxy-4,6,15-androstatriene[17(β-1')-spiro-5']perhydrofuran-2'-one.

13.5 g. of 3,3-ethylenedioxy-4,6,15-androstatriene-[17(β-1')-spiro-5']perhydrofuran-2'-one is dissolved in 650 ml. of absolute tetrahydrofuran, cooled in an ice bath, and then combined under agitation with 2.9 g. of lithium alanate and agitated for another 30 minutes while continuing the cooling. The excess reagent is then decomposed with water, the reaction solution is diluted with methylene chloride, washed with 2 N sulfuric acid and water, dried, and evaporated under vacuum. The residue is chromatographed on silica gel, thus obtaining 5.1 g. of 17β-hydroxy-17α-(3-hydroxypropyl)-4,6,15-androstatrien-3-one.

UV: $\epsilon_{285} = 25,200$.

EXAMPLE 2

420 mg. of 17β-hydroxy-17α-(3-hydroxypropyl)-4,6,15-androstatrien-3-one is agitated in 8.4 ml. of methanol and 1.68 ml. of water for 17 hours at 50° with 0.84 ml. of thioacetic acid. The mixture is then diluted with methylene chloride, washed with sodium bicarbonate solution and water, dried, and evaporated under vacuum. The residue is purified by preparative layer chromatography. Recrystallization from diisopropyl ether/acetone yields 320 mg. of 7α-acetylthio-17β-hydroxy- 17α-(3-hydroxypropyl)-4,15-androstadien-3-one, m.p. 138.5°–140°.

UV: $\epsilon_{238} = 18,200$.

EXAMPLE 3

150 mg. of 7α-acetylthio-17β-hydroxy-17α-(3-hydroxypropyl)-4,15-androstadien-3-one is allowed to stand in 0.5 ml. of pyridine with 0.3 ml. of acetic anhydride for 18 hours at room temperature. The mixture is then diluted with ether, washed with sodium bicarbonate solution and water, dried, and evaporated under vacuum. The residue is purified by preparative layer chromatography, thus obtaining 115 mg. of 17α-(3-acetoxypropyl)-7α-acetylthio-17β-hydroxy-4,15-androstadien-3-one.

UV: $\epsilon_{238} = 17,800$.

EXAMPLE 4

500 mg. of 17β-hydroxy-17α-(3-hydroxypropyl)-4,6,15-androstatrien-3-one is stirred in 10 ml. of methanol and 2 ml. of water with 1 ml. of thiopropionic acid for 17 hours at 50°. The mixture is then worked up as described in Example 2. After purification by preparative layer chromatography, 410 mg. of 17β-hydroxy-17α-(3-hydroxypropyl)-7α-propionylthio-4,15-androstadien-3-one is obtained.

UV: $\epsilon_{238} = 17,600$.

EXAMPLE 5

1.0 g. of 17β-hydroxy-17α-(3-hydroxypropyl)-4,6,15-androstatrien-3-one is agitated in 10 ml. of pyridine with 1 g. of succinic anhydride for 48 hours at room temperature. The mixture is then diluted with ether, washed with water, dried, and evaporated under vacuum. The residue is chromatographed on silica gel, thus obtaining 850 mg. of 17β-hydroxy-17α-(3-hydroxysuccinyloxypropyl)-4,6,15-androstatrien-3-one.

UV: $\epsilon_{285} = 24,500$.

600 mg. of 17β-hydroxy-17α-(3-hydroxysuccinyloxypropyl)-4,6,15-androstatrien-3-one is combined in 40 ml. of absolute methanol with an approximately 0.1 N methanolic ammonia solution until the point of equivalence has been reached. The reaction solution is then extensively concentrated under vacuum and precipitated in ice-cold absolute ether. The precipitate is vacuum-filtered, washed with absolute ether, and dried, thus producing 350 mg. of 17β-hydroxy-17α-(3-hydroxysuccinyloxypropyl)-4,6,15-androstatrien-3-one as the ammonium salt.

UV: $\epsilon_{285} = 24,600$.

EXAMPLE 6

2.1 g. of trimethyl sulfoxonium iodide is agitated in 40 ml. of dimethyl sulfoxide with 390 mg. of 55% sodium hydride oil suspension for 1.5 hours at room temperature. Under a nitrogen atmosphere, 1.5 g. of 17β-hydroxy-17α-(3-hydroxypropyl)-4,6,15-androstatrien-3-one is added to this solution, and the latter is stirred for 24 hours at room temperature. After precipitation into ice water, the precipitate is filtered off, washed with water, taken up in methylene chloride, dried, and evaporated. The residue is purified by repeated preparative layer chromatography, thus obtaining 350 mg. of 17β-hydroxy-17α-(3-hydroxypropyl)-6β,7β-methylene-4,15-androstadien-3-one.

UV: $\epsilon_{266} = 18,000$.

EXAMPLE 7

2.0 g. of 17β-hydroxy-17α-(3-hydroxypropyl)-15α,16α-methylene-4,6-androstadien-3-one is combined in 40 ml. of methanol and 8 ml. of water with 4 ml. of thioacetic acid and agitated for 18 hours at 50°. The mixture is diluted with ether, washed with sodium bicarbonate solution and water, dried, and evaporated under vacuum. The residue is chromatographed on silica gel. After recrystallization from diisopropyl ether/acetone, 1.4 g. of 7α-acetylthio-17β-hydroxy-17α-(3-hydroxypropyl)-15α,16α-methylene-4-androsten-3-one is obtained, m.p. 209°–210.5°.

UV: $\epsilon_{238} = 17,700$.

EXAMPLE 8

250 mg. of 7α-acetylthio-17β-hydroxy-17α-(3-hydroxypropyl)-15α,16α-methylene-4-androsten-3-one is allowed to stand in 1 ml. of pyridine and 0.5 ml. of acetic anhydride for 5 hours at room temperature. After ice water precipitation, the precipitate is filtered off, taken up in ether, washed with water, dried, and evaporated. The residue is purified by preparative layer chromatography, thus producing 185 mg. of 17α-(3-acetoxypropyl)-7α-acetylthio-17β-hydroxy-15α,16α-methylene-4-androsten-3-one.

UV: $\epsilon_{238} = 17,400$.

EXAMPLE 9

250 mg. of 7α-acetylthio-17β-hydroxy-17α-(3-hydroxypropyl)-15α,16α-methylene-4-androsten-3-one is allowed to stand in 1 ml. of pyridine and 0.5 ml. of butyric anhydride for 24 hours at room temperature. The mixture is diluted with ether, washed with water, dried, and evaporated to dryness under vacuum. The residue is purified by preparative layer chromatography, thus obtaining 205 mg. of 7α-acetylthio-17α-(3-butyryloxypropyl)-17β-hydroxy-15α,16α-methylene-4-androsten-3-one as an oil.

UV: $\epsilon_{238} = 17,100$.

EXAMPLE 10

500 mg. of 17β-hydroxy-17α-(3-hydroxypropyl)-15α,16α-methylene-4,6-androstadien-3-one is stirred in 5 ml. of methanol and 1 ml. of water with 1 ml. of thiopropionic acid for 24 hours at 50°. The mixture is diluted with ether, washed with sodium bicarbonate solution and water, dried, and evaporated under vacuum. The residue is purified by preparative layer chromatography, thus obtaining 310 mg. of 17β-hydroxy-17α-(3-hydroxypropyl)-15α,16α-methylene-7α-propionylthio-4-androsten-3-one.

UV: $\epsilon_{238} = 17,500$.

EXAMPLE 11

600 mg. of 17β-hydroxy-17α-(3-hydroxypropyl)-15α,16α-methylene-4,6-androstadien-3-one is heated under reflux in 6 ml. of pyridine with 600 mg. of succinic anhydride for 30 minutes. The mixture is diluted with ether, washed with water, dried, and evaporated under vacuum. The residue is chromatographed on silica gel, thus obtaining 580 mg. of 17β-hydroxy-17α-(3-hydroxysuccinyloxypropyl)-15α,16α-methylene-4,6-androstadien-3-one as an oil.

UV: $\epsilon_{285} = 23,500$.

250 mg. of 17β-hydroxy-17α-(3-hydroxysuccinyloxypropyl)-15α,16α-methylene-4,6-androstadien-3-one is dissolved in 25 ml. of absolute methanol and reacted with 0.1 N methanolic potassium methylate solution until the point of equivalence has been reached. The reaction solution is concentrated under vacuum to about 5 ml. and precipitated in absolute ether. The precipitate is vacuum-filtered, washed with absolute ether, and dried, thus obtaining 210 mg. of 17β-hydroxy-17α-(3-hydroxysuccinyloxypropyl)-15α,16α-methylene-4,6-androstadien-3-one as the potassium salt.

UV: $\epsilon_{285} = 25,100$.

EXAMPLE 12

250 mg. of 17β-hydroxy-17α-(3-hydroxysuccinyloxypropyl)-15α,16α-methylene-4,6-androstadien-3-one is reacted as described in Example 7 with 0.1 N methanolic sodium methylate solution and worked up, thus obtaining 185 mg. of 17β-hydroxy-17α-(3-hydroxysuccinyloxypropyl)-15α,16α-methylene-4,6-androstadien-3-one as the sodium salt.

UV: $\epsilon_{284} = 24,800$.

EXAMPLE 13

1.4 g. of trimethyl sulfoxonium iodide is stirred in 28 ml. of dimethyl sulfoxide with 171 mg. of 80% sodium hydride oil suspension for 2 hours at room temperature. Under nitrogen, 1.0 g. of 17β-hydroxy-17α-(3-hydroxypropyl)-15α,16α-methylene-4,6-androstadien-3-one is added to the almost clear solution, and the mixture is stirred for 24 hours at room temperature. The mixture is then introduced into ice water under agitation; the precipitate is filtered off, washed with water, and taken up in methylene chloride. After drying and evaporation, the residue is purified by repeated preparative layer chromatography, thus producing 130 mg. of 17β-hydroxy-17α-(3-hydroxypropyl)-6β,7β;15α,16α-dimethylene-4-androsten-3-one.

UV: $\epsilon_{265} = 17,500$.

EXAMPLE 14

10.0 g. of 15β,16β-methylene-3-oxo-4,6-androstadiene-[17(β-1')-spiro-5']perhydrofuran-2'-one is combined in 50 ml. of methylene chloride with 30 ml. of ethylene glycol, 20 ml. of the triethyl ester of orthoformic acid, and 300 mg. of p-toluenesulfonic acid and stirred for 75 minutes at 50°. Then, 3 ml. of pyridine is added to the reaction solution; the latter is diluted with ether, washed with water, dried, and evaporated to dryness under vacuum, thus obtaining 12 g. of crude 3,3-ethylenedioxy-15β,16β-methylene-4,6-androstadiene[17(β-1')-spiro-5']perhydrofuran-2'-one.

12 g. of 3,3-ethylenedioxy-15β,16β-methylene-4,6-androstadiene[17(β-1')-spiro-5']perhydrofuran-2'-one is dissolved in 600 ml. of absolute tetrahydrofuran, cooled in an ice bath, combined under agitation with 2.75 g. of lithium alanate, and stirred for 30 minutes at ice bath temperature. The excess reagent is decomposed with water, and the reaction solution is diluted with methylene chloride. The mixture is washed with 2 N sulfuric acid and water, dried, and evaporated to dryness under vacuum. After chromatography on silica gel, 4.5 g. of 17β-hydroxy-17α-(3-hydroxypropyl)-15β,16β-methylene-4,6-androstadien-3-one is obtained. A sample recrystallized from diisopropyl ether/acetone melts at 200°-201.5°.

UV: $\epsilon_{285} = 25,500$.

EXAMPLE 15

500 mg. of 17β-hydroxy-17α-(3-hydroxypropyl)-15β,16β-methylene-4,6-androstadien-3-one is stirred in 10 ml. of methanol and 2 ml. of water with 1 ml. of thioacetic acid for 17 hours at room temperature. The mixture is then diluted with ether, washed with sodium bicarbonate solution and water, dried, and evaporated under vacuum. The residue is purified by preparative layer chromatography and recrystallized from diisopropyl ether/acetone, thus obtaining 350 mg. of 7α-acetylthio-17β-hydroxy-17α-(3-hydroxypropyl)-15β,16β-methylene-4-androsten-3-one, m.p. 206°-208°.

UV: $\epsilon_{238} = 18,800$.

EXAMPLE 16

100 mg. of 7α-acetylthio-17β-hydroxy-17α-(3-hydroxypropyl)-15β,16β-methylene-4-androsten-3-one is allowed to stand in 0.5 ml. of pyridine with 0.2 ml. of propionic anhydride for 18 hours at room temperature. The reaction solution is diluted with ether, washed with sodium bicarbonate solution and water, dried, and evaporated under vacuum. The residue is purified by preparative layer chromatography, thus producing 65 mg. of 7α-acetylthio-17β-hydroxy-17α-(3-propionyloxypropyl)-15β,16β-methylene-4-androsten-3-one.

UV: $\epsilon_{238} = 18,600$.

EXAMPLE 17

200 mg. of 17β-hydroxy-17α-(3-hydroxypropyl)-15β,16β-methylene-4,6-androstadien-3-one is allowed to stand in 4 ml. of methanol and 0.8 ml. of water with 0.4 ml. of thiopropionic acid for 24 hours at room temperature. The mixture is worked up as described in Example 11. After purification by preparative layer chromatography, 145 mg. of 17β-hydroxy-17α-(3-hydroxypropyl)-15β,16β-methylene-7α-propionylthio-4-androsten-3-one is obtained.

UV: $\epsilon_{237} = 18,100$.

EXAMPLE 18

1.0 g. of 17β-hydroxy-17α-(3-hydroxypropyl)-15β,16β-methylene-4,6-androstadien-3-one is allowed to stand in 10 ml. of pyridine with 1.0 g. of succinic anhydride for 48 hours at room temperature. The mixture is diluted with ether, washed with water, dried, and evaporated under vacuum. The residue is chromatographed on silica gel, thus obtaining 720 mg. of 17β-hydroxy-17α-(3-hydroxysuccinyloxypropyl)-15β,16β-methylene-4,6-androstadien-3-one as an oil.

UV: $\epsilon_{285} = 24,700$.

500 mg. of 17β-hydroxy-17α-(3-hydroxysuccinyloxypropyl)-15β,16β-methylene-4,6-androstadien-3-one is dissolved in 35 ml. of absolute methanol and reacted with 0.1 N methanolic potassium methylate solution until the point of equivalence has been reached. The reaction solution is then extensively concentrated under vacuum and precipitated into ice-cold absolute ether. The precipitate is vacuum-filtered, washed with absolute ether, and dried, thus obtaining 420 mg. of 17β-hydroxy-17α-(3-hydroxysuccinyloxypropyl)-15β,16β-methylene-4,6-androstadien-3-one as the potassium salt.

UV: $\epsilon_{285} = 24,500$.

EXAMPLE 19

2.1 g. of trimethyl sulfoxonium iodide is stirred in 40 ml. of dimethyl sulfoxide with 390 mg. of 55% sodium hydride oil suspension for 1.5 hours at room temperature. Under nitrogen, 1.5 g. of 17β-hydroxy-17α-(3-hydroxypropyl)-15β,16β-methylene-4,6-androstadien-3-one is added to this solution, and the latter is stirred at room temperature for 24 hours. After ice water precipitation, the precipitate is filtered off, washed with water, and taken up in methylene chloride. After drying and evaporation, the residue is purified by repeated preparative layer chromatography, thus obtaining 220 mg. of 17β-hydroxy-17α-(3-hydroxypropyl)-6β,7β;15β,16β-dimethylene-4-androsten-3-one.

UV: ε₂₆₆=17,900.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 17β-Hydroxy-4-androsten-3-one of Formula I

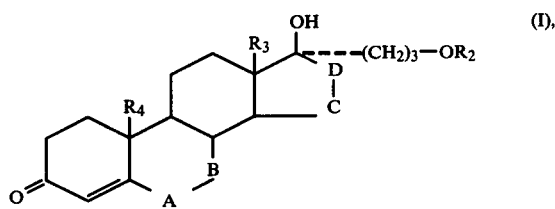

wherein
R₂ is hydrogen or the monovalent acyl radical of a monobasic or dibasic hydrocarbon carboxylic acid of up to 18 carbon atoms;
R₃ is methyl or ethyl;
R₄ is hydrogen or methyl;

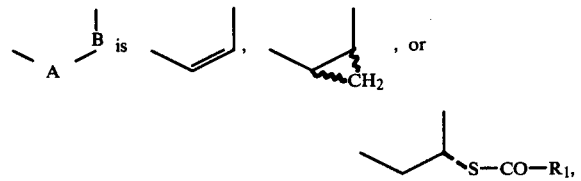

wherein R₁ is lower alkyl; and

and when R₂ is the acyl radical of a dibasic acid, the physiologically acceptable salts thereof with the free acid moiety of the R₂ group.

2. 17β-Hydroxy-17α-(3-hydroxypropyl)-4,6,15-androstatrien-3-one, a compound of claim 1.

3. 7α-Acetylthio-17β-hydroxy-17α-(3-hydroxypropyl)-4,15-androstadien-3-one, a compound of claim 1.

4. 17α-(3-Acetoxypropyl)-7α-acetylthio-17β-hydroxy-4,15-androstadien-3-one, a compound of claim 1.

5. 7α-Propionylthio-17β-hydroxy-17α-(3-hydroxypropyl)-4,15-androstadien-3-one, a compound of claim 1.

6. 17β-Hydroxy-17α-(3-hydroxysuccinyloxypropyl)4,6,15-androstatrien-3-one, a compound of claim 1.

7. Ammonium salt of 17β-hydroxy-17α-(3-hydroxysuccinyloxypropyl)-4,6,15-androstatrien-3-one, a compound of claim 1.

8. 17β-Hydroxy-17α-(3-hydroxypropyl)-6β,7β-methylene-4,15-androstadien-3-one, a compound of claim 1.

9. 17β-Hydroxy-17α-(3-hydroxypropyl)-15α,16α-methylene-4-androsten-3-one, a compound of claim 1.

10. 17β-Hydroxy-17α-(3-hydroxypropyl)-15α,16α-methylene-4,6-androstadien-3-one, a compound of claim 1.

11. 7α-Acetylthio-17β-hydroxy-17α-(3-hydroxypropyl)-15α,16α-methylene-4-androsten-3-one, a compound of claim 1.

12. 17α-(3-Acetoxypropyl)-7α-acetylthio-17β-hydroxy-15α,16α-methylene-4-androsten-3-one, a compound of claim 1.

13. 7α-Acetylthio-17α-(3-butyryloxypropyl)-17β-hydroxy-15α,16α-methylene-4-androsten-3-one, a compound of claim 1.

14. 17β-Hydroxy-17α-(3-hydroxypropyl)-15α,16α-methylene-7α-propionylthio-4-androsten-3-one, a compound of claim 1.

15. 17β-Hydroxy-17α-(3-hydroxysuccinyloxypropyl)-15α,16α-methylene-4,6-androstadien-3-one, a compound of claim 1.

16. 17β-Hydroxy-17α-(3-hydroxysuccinyloxypropyl)-15α,16α-methylene-4,6-androstadien-3-one potassium salt, a compound of claim 1.

17. 17β-Hydroxy-17α-(3-hydroxysuccinyloxypropyl)-15α,16α-methylene-4,6-androstadien-3-one sodium salt, a compound of claim 1.

18. 17β-Hydroxy-17α-(3-hydroxypropyl)-6β,7β;-15α,16α-dimethylene-4-androsten-3-one, a compound of claim 1.

19. 17β-Hydroxy-17α-(3-hydroxypropyl)-15β,16β-methylene-4,6-androstadien-3-one, a compound of claim 1.

20. 7α-Acetylthio-17β-hydroxy-17α-(3-hydroxypropyl)-15β,16β-methylene-4-androsten-3-one, a compound of claim 1.

21. 7α-Acetylthio-17β-hydroxy-17α-(3-propionyloxypropyl)-15β,16β-methylene-4-androsten-3-one, a compound of claim 1.

22. 17β-Hydroxy-17α-(3-hydroxypropyl)-15β,16β-methylene-7α-propionylthio-4-androsten-3-one, a compound of claim 1.

23. 17β-Hydroxy-17α-(3-hydroxysuccinyloxypropyl)-15β,16β-methylene-4,6-androstadien-3-one, a compound of claim 1.

24. 17β-Hydroxy-17α-(3-hydroxysuccinyloxypropyl)-15β,16β-methylene-4,6-androstadien-3-one potassium salt, a compound of claim 1.

25. 17β-Hydroxy-17α-(3-hydroxypropyl)-6β,7β;15β,16β-dimethylene-4-androsten-3-one, a compound of claim 1.

26. A pharmaceutical composition comprising a diuretically effective amount of a compound of claim 1 and a pharmaceutically acceptable carrier.

27. The pharmaceutical composition of claim 26, wherein the amount of active ingredient is 10-100 mg.

28. A method of reversing the effect of desoxycorticosterone on the elimination of potassium and sodium which comprises administering a diuretically effective amount of a compound of claim 1.

* * * * *

UNITED STATES PATENT AND TRADEMARK OFFICE
CERTIFICATE OF CORRECTION

PATENT NO. : 4,180,570
DATED : December 25, 1979
INVENTOR(S) : RUDOLF WIECHERT ET AL It is certified that error appears in the above-identified patent and that said Letters Patent are hereby corrected as shown below:

IN THE ABSTRACT, THE FORMULAE SHOULD READ AS FOLLOWS:

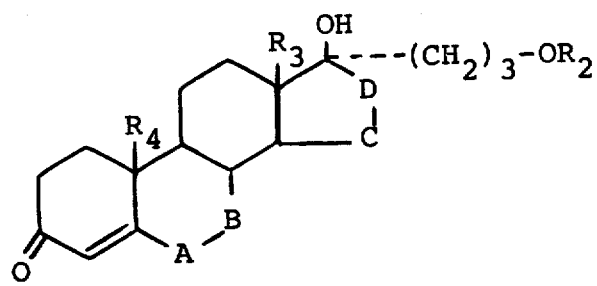

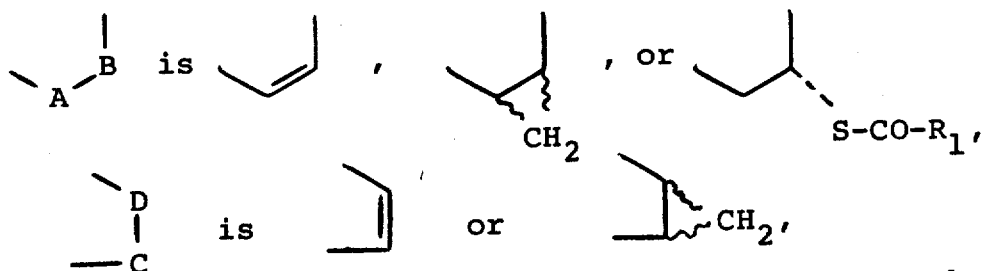

Signed and Sealed this

Tenth Day of June 1980

[SEAL]

Attest:

SIDNEY A. DIAMOND

Attesting Officer     Commissioner of Patents and Trademark